United States Patent [19]

Abdelqader

[11] Patent Number: 5,397,892
[45] Date of Patent: Mar. 14, 1995

[54] FIBER OPTIC LIGHT SOURCE FOR A DENTAL CURING LAMP WITH TWO PEGS FOR REMOVABLY ALIGNING THE SOURCE WITH AN INTENSITY DETECTOR

[75] Inventor: Steven Abdelqader, Thiells, N.Y.

[73] Assignee: Coltene/Whaledent, Inc., Mahwah, N.J.

[21] Appl. No.: 178,776

[22] Filed: Jan. 7, 1994

[51] Int. Cl.6 .......................... H01J 5/16; H01J 40/14
[52] U.S. Cl. ................................. 250/227.24; 433/29
[58] Field of Search ................. 250/227.11, 227.24, 250/239; 385/88, 89, 92, 115, 139; 433/229, 29, 32

[56] References Cited

U.S. PATENT DOCUMENTS

| | | | |
|---|---|---|---|
| 4,397,523 | 8/1983 | Feinbloom et al. | 350/96.20 |
| 4,450,139 | 5/1984 | Bussiere et al. | 422/186.3 |
| 4,605,280 | 8/1986 | Welber et al. | 350/96.20 |
| 4,632,504 | 12/1986 | Thillays | 350/96.20 |
| 4,647,147 | 3/1987 | Pikulski et al. | 350/96.17 |
| 4,768,199 | 8/1988 | Heinen et al. | 372/36 |
| 5,147,204 | 9/1992 | Patten et al. | 433/229 |
| 5,208,888 | 5/1993 | Steinblatt et al. | 385/90 |

Primary Examiner—David C. Nelms
Assistant Examiner—Steven L. Nichols
Attorney, Agent, or Firm—Helfgott & Karas

[57] ABSTRACT

A fiber optic light detector for determining the light intensity of a light emitted from a light source. The device includes a photocell, a light intensity display and two stationary pegs. The two pegs are spacedly positioned about the periphery of the photocell. When measuring light intensity, a fiber optic bundle illuminated by a light source is positioned to cover the photocell and be in contact with both of the two pegs. When the light source is positioned in this manner, complete coverage of the photocell is ensured regardless of the size of the fiber optic bundle. The light intensity display displays the digital value of the intensity determined by the photocell. The light detector is also adapted for connection and concurrent operation with a light source, i.e. a curing light.

20 Claims, 5 Drawing Sheets

FIBER OPTIC LIGHT SOURCE FOR A DENTAL CURING LAMP WITH TWO PEGS FOR REMOVABLY ALIGNING THE SOURCE WITH AN INTENSITY DETECTOR

BACKGROUND OF THE INVENTION

1. Field of the Invention

This invention relates generally to fiber optic light detectors and, more particularly, to fiber optic light detectors on which a fiber optic bundle can be accurately placed to completely cover the photocell in the detector.

2. Description of the Prior Art

The use of fiber optic bundles is relatively widespread, especially in the fields of medicine and dentistry. The fiber optic bundle in conjunction with a light source is generally known as a cold light source. In the medical/dental field, the fiber optic bundle is used to direct light at an area under investigation. The fiber optic can be in the form of a plurality of individual strands formed together into a sheath, or a single rod encased in a sheath. Both of these will hereinafter be referred to as fiber optic bundles.

Basically, a fiber optic light source comprises a fiber optic bundle which is illuminated by a high intensity, high wattage lamp. The fiber optic bundle may be several feet long and is positioned in a housing with respect to the lamp so that the filament of the lamp transfers maximum light to the fiber optic bundle. The fiber optic bundle is used to direct light from the light source to any desired position. A dentist might use the fiber optic light source to aid in curing material used to repair teeth. For such use, light of a specific intensity is needed.

Various manufacturers make fiber optic bundles of different diameters. The typical diameter of such bundles can vary between 3/32" to ½" or more.

Fiber optic light detectors are generally well known and are used for sensing the light intensity of fiber optic bundles illuminated by a light source. The fiber optic light detector contains a photocell. A fiber optic bundle, whose intensity is desired to be measured, is placed to cover the photocell. When the photocell is covered it measures the light intensity of the fiber optic bundle. To obtain an accurate reading, the photocell should be completely covered.

Prior attempts at completely covering the photocell are illustrated in FIGS. 1 and 2. FIG. 1 illustrates a device in which a target was placed around the photocell 52. This represents a bull's eye target 62, with the photocell 52 being the bull's eye. The fiber optic bundle illuminated by the lamp of a light source is then placed over the bull's eye target 62 in a manner to cover the photocell 52. The circles surrounding the photocell 52 are provided as guides for correctly positioning the fiber optic bundle. The different sized circles in the target account for alignment with different sized fiber optic bundles. This device does not include components which will aid in holding fiber optic bundles in a position in which they will cover the photocell for the period necessary to obtain an accurate reading of the light intensity. The fiber optic bundles are therefore apt to move and if not covering the photocell will produce an inaccurate reading.

FIG. 2 illustrates another approach using a step device. The photocell 52 is positioned at the bottom of a well 64 with steps 66 surrounding the photocell 52 leading out of the well 64. A fiber optic bundle is then placed over the well 64 at the deepest level to which it can fit based on the size of the fiber optic bundle. The light source is then activated and an intensity reading is taken by the photocell 52. If the fiber optic bundle does not fit snugly into a step, it is apt to slide around within the step and distort the reading. Another problem with such a device is that the steps provide a distance between the fiber optic bundle and the photocell. This distance can result in an erroneous measurement.

An example of an apparatus for accommodating various diameter fiber optic bundles is described in U.S. Pat. No. 4,397,523 issued Aug. 9, 1983. This patent describes an arrangement whereby the fiber optic bundle will be centrally positioned with respect to a light. It uses three movable pins, each at 120° around a central axis which can move radially in and out as a surrounding knob is rotated. These pins maintain the central position of the fiber optic bundle regardless of its diameter by adjusting the inward and outward movement of these pins. This device is used for clamping a fiber optic bundle to a light source. Another example of a device for positioning a fiber optic with respect to a light source is shown in U.S. Pat. No. 4,768,199 issued Aug. 30, 1988. This patent uses a "V" groove for positioning the fiber optic so that it will be co-axial with a laser light.

Although these devices attempt to sense the light intensity of fiber optic bundles and are adapted for positioning of fiber optic bundles to cover a photocell or light source, they are not necessarily very accurate. They do not provide a device which will insure complete coverage of the photocell while sensing the intensity of the light source. These devices thus allow for the possible introduction of ambient light when the photocell is not completely covered. Certain of these devices also allow for a distance between the photocell and the fiber optic bundle. Due to this distance, the intensity of the light is diminished at the point of the photocell.

It is, therefore, needed to produce a fiber optic light detector which solves the aforementioned problems and provides improvements over the presently known devices for measuring the intensity of a light source.

SUMMARY OF THE INVENTION

It is, accordingly, an object of the present invention to produce a fiber optic light detector which will accurately measure the intensity of a light source.

It is a further object of the present invention to produce a fiber optic light detector which allows for complete coverage of the photocell by the fiber optic bundle.

It is an even further object of the present invention to produce a fiber optic light detector which eliminates the space between the photocell and the fiber optic bundle whose intensity is being measured.

A still further object of the present invention is to account for all sizes of fiber optic bundles which will completely cover the photocell.

An even further object of the present invention is to produce a fiber optic light detector having two permanently installed stationary pegs strategically placed about the photocell so that, when a fiber optic bundle is placed in contact with the two pegs, the photocell is completely covered, regardless of the size of the fiber optic bundle.

A still further object of the present invention is to produce a fiber optic light detector adapted to be connected with a light source for concurrent operation of both devices using the same power supply.

The present invention includes a photocell, a light intensity display and two permanently positioned pegs strategically secured about the photocell. The photocell is generally known and is used to sense light from a light source and determine the intensity of that light. The photocell then sends this information to the light intensity display which produces a digital display of the intensity of the light from the light source being measured. The two pegs positioned around the photocell are arranged so that, when the fiber optic bundles are positioned to touch both pegs and cover the photocell, the entire photocell will be covered by the fiber optic bundle, regardless of the size of the bundle. The two pegs also act as a support for the fiber optic bundles, aiding in holding them in place over the photocell for the period necessary to obtain an accurate intensity reading. This device is adapted for connection and concurrent operation with a light source, i.e. a curing light, and also includes a time dial for setting a desired amount of time during which the light source is operational. The light source is connected to the fiber optic light detector and a common power supply is used to power both the light detector and the light source.

The aforementioned objects, features and advantages of the invention will, in part, become obvious from the following more detailed description of the invention, when taken in conjunction with the accompanying drawings, which form an integral part thereof.

DETAILED DESCRIPTION OF THE PREFERRED EMBODIMENT

Figure 4:
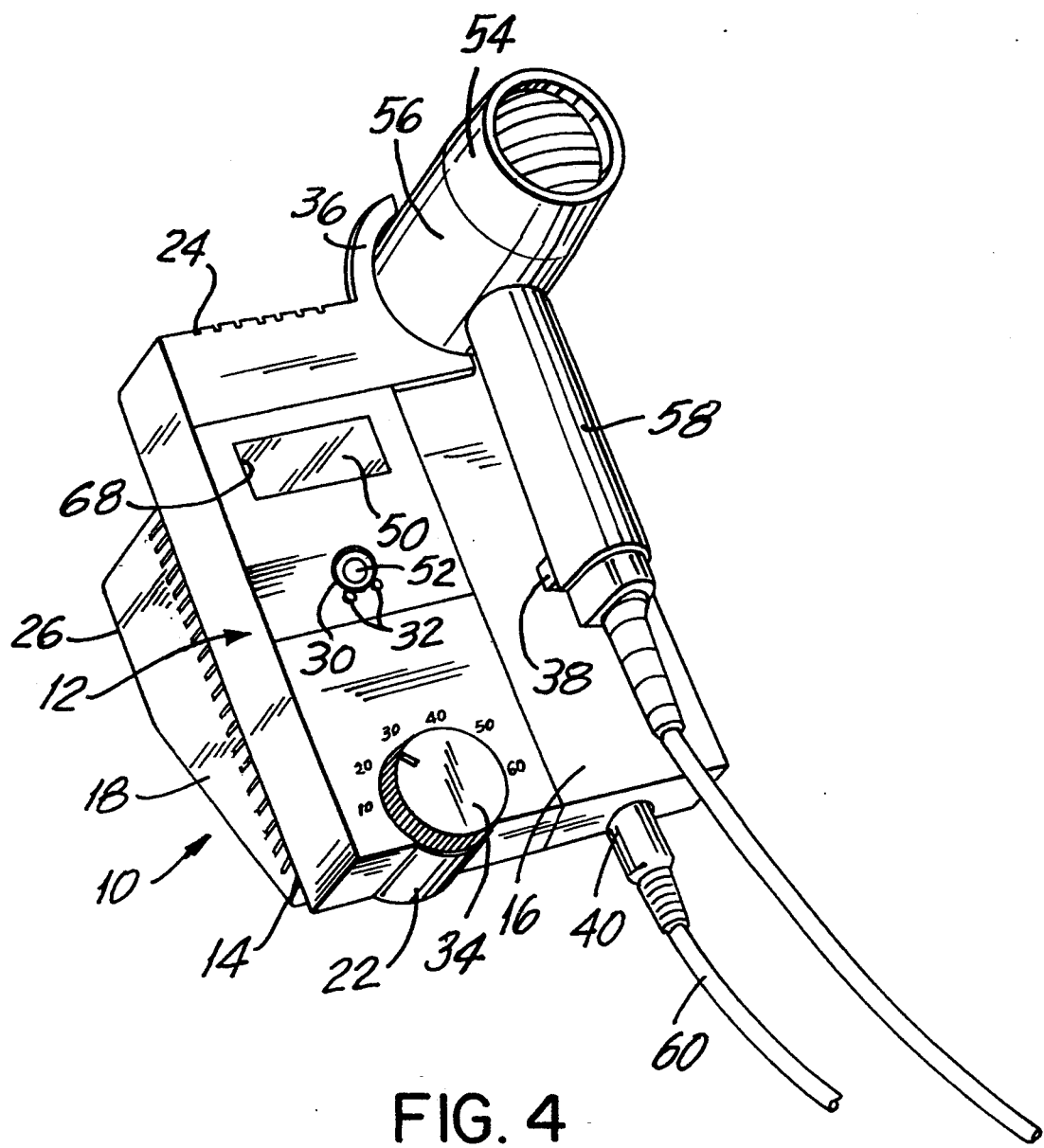
FIG. 4 is a perspective view of the fiber optic light detector of the present invention connected with a dental curing light.
Figure 5:
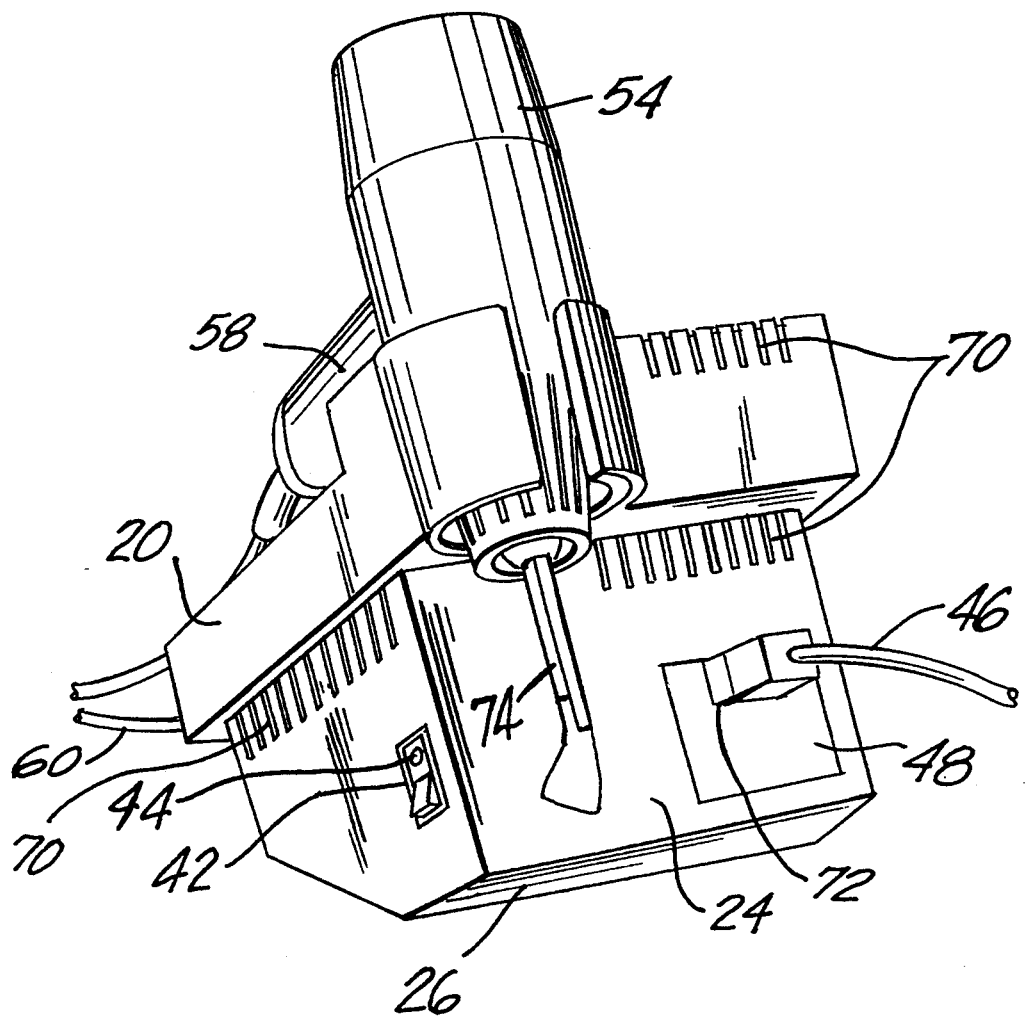
FIG. 5 is a perspective side view of the fiber optic light detector of the present invention connected with the dental curing light shown in FIG. 4.
Figure 6:
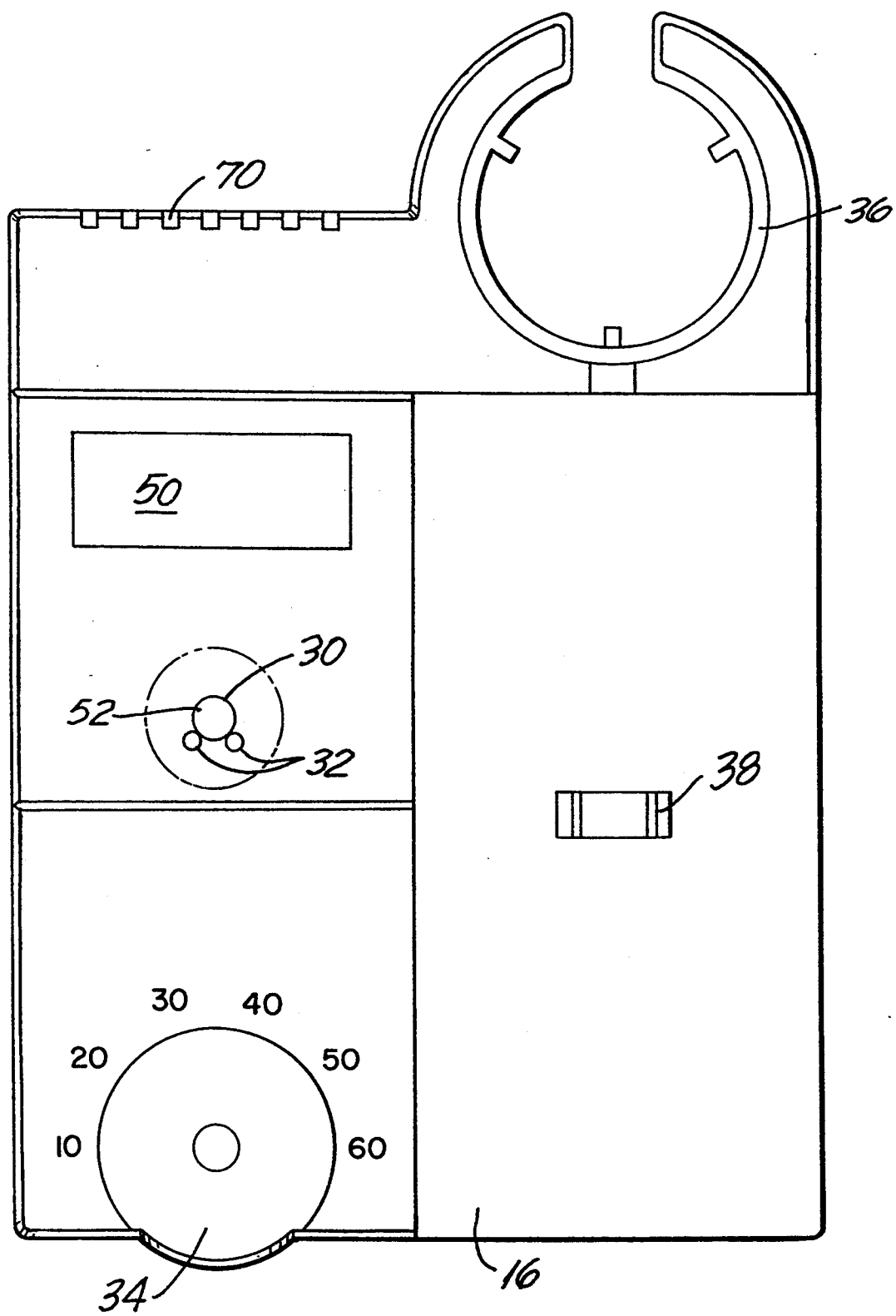
FIG. 6 is a top view of the fiber optic light detector of the present invention.

Referring now to FIGS. 4—6, a fiber optic light detector will now be described. The light detector is illustrated generally by the number 10 and, as shown in FIGS. 4 and 5, is connected with a curing light 54. It includes a housing 12 having base side 14, a face side 16, left and right opposing side walls 18 and 20 respectively, a lower end 22 and the upper end 24. Extending between the base 14 and the upper end 24 is an intermediary wall 26.

The base 14 is flat and extends at an angle with the face 16, as can best be seen in FIG. 5. The base 14 includes feet (not shown) on which the device 10 stands. On the face 16, as is shown in FIG. 6, there is a digital readout 68. Within the housing 12, at a position where it can be easily read through the readout 68, is a liquid crystal display 50. Proximate this readout 68 is a circular aperture 30. Also within the housing 12 and positioned where it may extend into the circular aperture 30 is a photocell 52. The photocell 52 is connected to the liquid crystal display 50 so that the liquid crystal display 50 may display a digital indication of readings sensed by the photocell 52.

Adjacent the circular aperture 30 are two stationary pegs 32. The two pegs 32 are for aiding in the positioning of fiber optic bundles to completely cover the photocell 52, as will be explained hereinafter. The photocell 52 is of a diameter which is small enough to be completely covered by any fiber optic bundle having a diameter equal to or greater than that of the photocell 52 when the fiber optic bundle is placed in a position touching the two pegs 32 and thereby covering the photocell 52.

Extending from the face 16 of the housing 12 is a dial 34. Printed on the face 16 at positions spaced around the dial 34 are indicia indicative of dial settings. The dial 34 acts as a timer, for setting the amount of time a light source connected to the device 10 is operational. The timer is set in intervals of 10 seconds up to a maximum of 60 seconds. Extending through the face 16 of the housing at a side adjacent with the upper end 24 is a cradle 36. The cradle 36 is for receiving a curing light 54 as is seen in FIGS. 4 and 5, to be used with this light detector. On the face 16, at a point in line with the cradle 36, is a seat 38 for resting a handle 58 of the curing light used with this device.

At the lower end 22 of the device is a connector 40 for connecting a cord 60 from the curing light 54, as can best be seen in FIG. 4. An eight pin connector is normally used for the connector 40. This allows for proper connection of the curing light 54. On the right opposing side wall is power button 42, as can be seen in FIG. 5. The power button 42 has a green indicator light 44. This indicator light 44 informs the user when the device is operating. At the upper end 24 is a receptacle 72 for receiving a power cord 46 and a fuse compartment 48. Extending around the left and right opposing side walls, the lower end and the upper end 18, 20, 22 and 24 respectively, are a number of vents 70. The vents 70 allow for passage of heat generated during operation to flow out of the housing 12.

Figure 1:
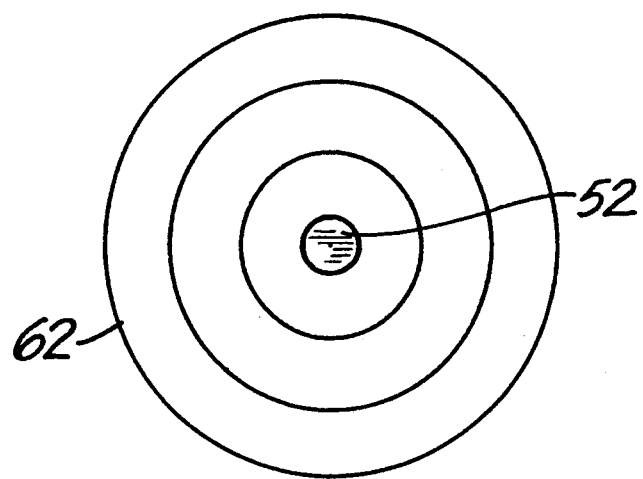
FIG. 1 illustrates a prior art photo detector having a bull's eye surrounding the photocell.
Figure 2:
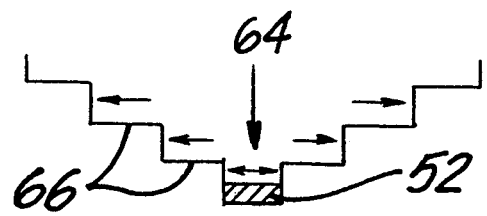
FIG. 2 illustrates a prior art photocell having steps surrounding the photocell.
Figure 3:
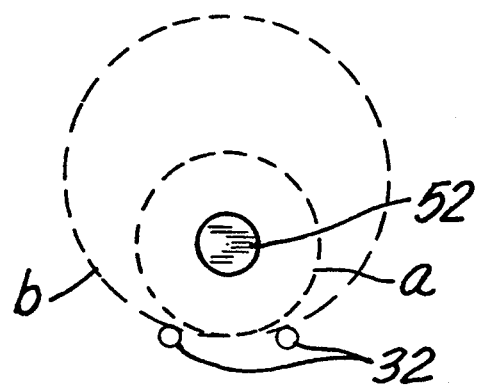
FIG. 3 illustrates the photocell of the present invention utilizing the two pegs.

FIG. 3 is an enlarged view of the photocell 52 and the two permanently installed stationary pegs 32. The pegs 32 extend from the face 16 and are circumferentially spaced about the photocell 52. The distance between the pegs 32 should be less than the diameter of the photocell 52. The pegs 32 may be positioned around any region of the photocell 52.

Optimally, the pegs 32 should be spread apart from one another and positioned slightly spaced outwardly from the periphery of the photocell 52. The optimal region around the periphery of the photocell on which the pegs 32 should be placed is on its bottom half, toward the lower end 22. Because of the incline at which the face side 16 is angled, this positioning of the pegs 32 on the lower half of the photocell 52 would allow the fiber optic bundle to rest against the pegs 32 instead of needing the user to apply upward or sideways pressure to hold the fiber optic bundles against the pegs 32. This positioning of the pegs 32 will also allow the detector to accommodate all sizes of fiber optic bundles. This is shown by the circular dotted lines in FIG. 3. Each circular dotted line represents a different sized fiber optic bundle. As can be seen, these lines encircle the photocell 52 indicating complete coverage of the photocell 52. Having the pegs 32 positioned a short distance removed from the periphery of the photocell 52 allows for placement of a bundle to ensure coverage of the photocell 52 at the point of the peg placement.

Having the pegs 32 slightly spread apart from one another further ensures complete coverage of the photocell 52 based on the arc of curvature of both the bundles and the photocell 52. It can be seen from FIG. 3 how the arc of curvature differs between the photocell 52 and the different sized bundles encircling the photocell 52. There is, although, a distinctive tangent point 76 where the arcs meet below the photocell 52.

The greater the arcuate spacing between the pegs 32, the smaller the range of sizes of fiber optic bundles the detector will accommodate. The larger the arcuate space between the pegs 32 the less apt a larger bundle will be able to extend between the pegs 32.

As the arcuate distance between the pegs 32 increases to equal the diameter of the photocell 52 the range of sizes of fiber optic bundles will decrease until, when the pegs 32 are separated by a distance equal to the diameter of the photocell 52, the only size fiber optic bundle which may be accommodated would be approximately equal to the size of the photocell 52 plus the slight spacing that the pegs extend beyond the periphery of the photocell circumference. This is because, when the pegs 32 are separated by such a distance, in order for the fiber optic bundle to completely cover the photocell and also touch both pegs, the bundle must fit between the two pegs. At the same time, the pegs should have some arcuate spacing between them to support the fiber optic bundle. Preferably, it has been found that the arcuate spacing between the pegs should be between 15° and 60°.

Because of the pegs 32 the photocell 52 will always be completely covered by the fiber optic bundle. The complete coverage of the photocell, in this manner, insures an accurate reading of the light intensity due to the elimination of ambient light entering the photocell and a lack of space between the fiber optic bundle and the photocell.

FIGS. 4 and 5 illustrate the fiber optic light detector of the present invention connected with a curing light 54. The handpiece 56 of the curing light 54 rests within the cradle 36. Connected to the handpiece 56 and extending below the cradle 36 is a light guide 74 which houses the fiber optic bundle. The handle 58 of the curing light 54 is positioned to contact the seat 38 and the cord 60 is inserted into the connector 40 at the foot 22 of the device. The curing light 54 also includes a trigger and an audible indicator (not shown). The trigger turns the curing light 54 on and off by depressing it towards the handle 58 and then releasing it. Each time the trigger is depressed, the audible indicator sounds.

Figure 7:
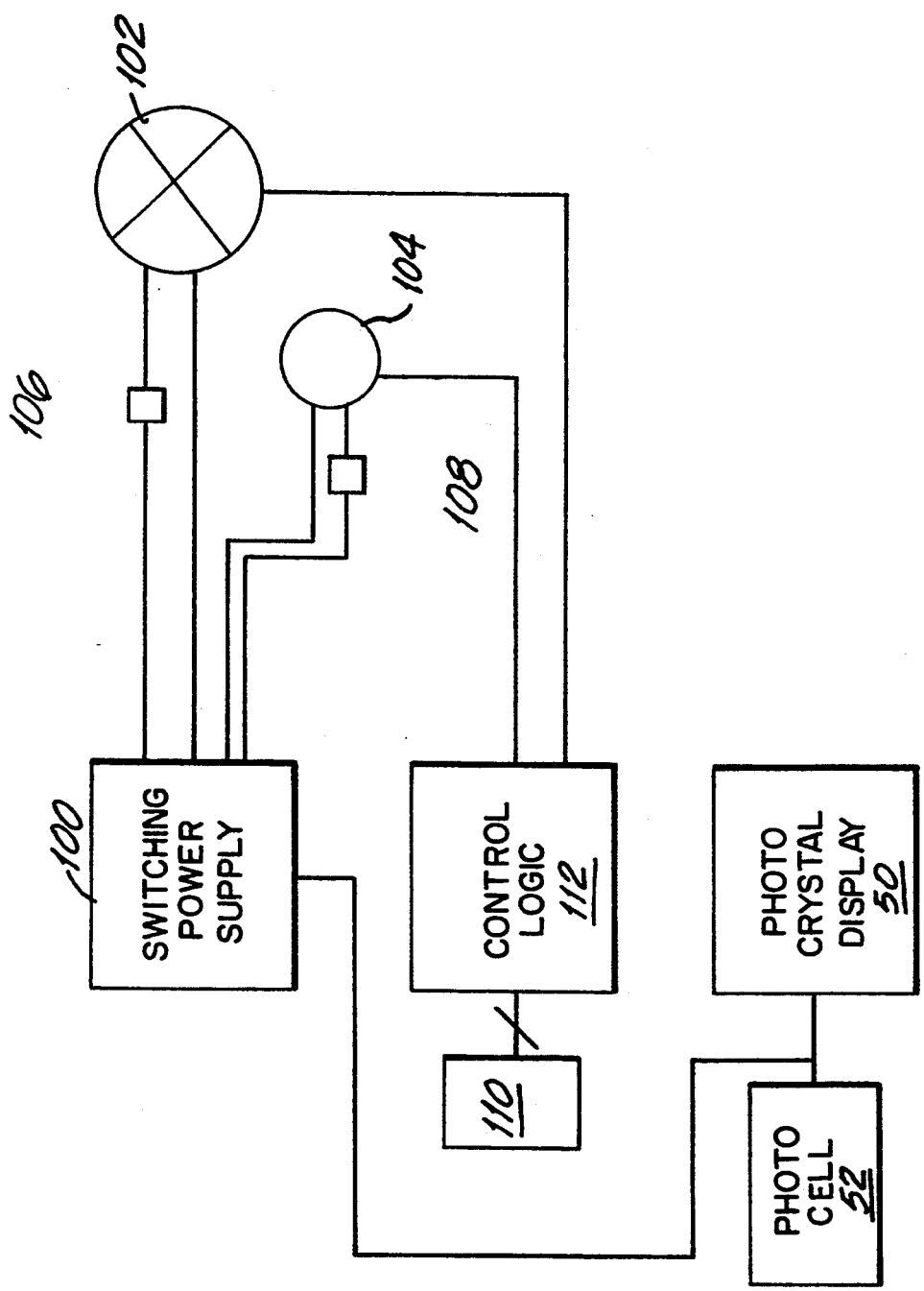
FIG. 7 is a block diagram of the internal components of the fiber optic light detector of the present invention connected with a curing light.

FIG. 7 illustrates a block diagram of the device combining the fiber optic light detector along with a light source. The device is connected through a power cord to an electrical socket which serves as the power supply 100. Power is supplied by the power supply 100 to both a halogen lamp 102 and a fan 104 in the light source. Connected between the power supply 100 and the halogen lamp 102 is a first thermal switch 106 and connected between the power supply 100 and the fan 104 is a second thermal switch 108. The first thermal switch 106 senses the temperature within the source and disconnects the halogen lamp 102 from the power supply 100 when either the source has been operating for a predetermined period of time or a first threshold temperature is reached, the threshold temperature being the temperature above the normal operating temperature and below a temperature at which a fuse will blow in the source. This switch 106 acts as a circuit breaker.

The second thermal switch 108 allows the fan 104, to operate for a period of time after the source has ceased operation and serves to turn the fan 104 off when a second threshold temperature is reached after use of the source. This thermal switch 108 allows the fan 104 to cool the source for a period of time after use.

Also connected to both the halogen lamp 102 and the fan 104 is a switch setting circuit 110 and a control logic circuit 112. The dial 34 controls the switch setting circuit 110. The control logic circuit 112 controls all the logical functions of the source. Included in these functions is turning off the source when a time set by the dial 34 expires and, when the audible sound occurs. As shown in the curing light of FIGS. 4 and 5, sounding of the audible indicator occurs each time the curing light is turned on and off, either manually or automatically.

Also connected to the power supply 100 are both the photocell 52 and the liquid crystal display 50 of the detector. The power supply 100 drives the photocell 52 to be able to accurately and quickly determine the light intensity of a light source. This information regarding the intensity of the light source is delivered to the liquid crystal display 50 where a digital indication of the intensity is displayed.

In operation, a power cord 46 is connected between an electrical socket and the receptacle 72 in the upper end 74 of the detector. A device may be connected to connector 40 for concurrent operation with the detector. The power button 42 is then switched to the "on" position. This is indicated by the green light 44 on the power button 42 being illuminated. The green light 44 is illuminated for as long as the power button 42 is in the "on" position. The fiber optic bundle is then placed in a position touching both of the pegs 32. When placed in this position, regardless of the size of the fiber optic bundle, it is able to completely cover the photocell 52. It is important that the photocell 52 is completely covered so that an accurate light intensity reading is obtained. Pressure is placed against the pegs 32 by the fiber optic bundle, wherein the pegs 32 act as a support for the fiber optic bundle, holding it in position over the photocell. This aids in holding the fiber optic bundle stationary and completely covering the photocell 52 for the time required to take an accurate reading. The pegs 32, therefore, act not only as a guide for positioning the bundle but also as a support and seat for holding the bundle in place covering the photocell 52. The light source is then activated and after ten seconds, to allow the meter to stabilize, a light intensity reading is displayed on the liquid crystal display 50. The liquid crystal display, therefore, informs the user whether the intensity of the light being used is high enough.

When a reading is too low it may indicate any of a number of problems. These problems include a blown fuse, a cracked or rough surface on the light filter, material cured to the tip of the light guide or even the need to replace the lamp bulb.

When used with a curing light, the light intensity is very important. If the light emanating from the curing light is not of a suitable intensity, restorations will not be fully cured when the curing light is operated for the normally required amount of time. The curing light will need to be applied to the restoration for an extended period. Without first determining the intensity of the light, this would not be known to the user.

It is to be understood that the fiber optic light detector of the present invention may be used with any type of light source. The use of this device with a curing light was for purposes of example only and not meant to limit the scope of this invention. Furthermore, the light source, of which a light intensity reading is desired, need not be connected to the light detector but may be operating independently of the light detector.

There has been disclosed heretofore the best embodiment of the invention presently contemplated. However, it is to be understood that various changes and modifications may be made thereto without departing from the spirit and scope of the invention.

I claim:

1. A fiber optic light detector for determining the intensity of a light emitted from a light source and transmitted through a fiber optic bundle, comprising:
    a photocell for sensing a light and determining the intensity of the light;
    a light intensity display, connected to the photocell, for displaying the intensity of the light determined by the photocell; and
    first and second stationary pegs integral with the light detector and spaced about the circumference of the photocell, against which the fiber optic bundle is removably positioned to thereby completely cover the photocell when determining the intensity of the light emitted through the fiber optic bundle.

2. The fiber optic light detector of claim 1, wherein the first and second stationary pegs are positioned about the photocell such that the distance between the first and second pegs is less than the diameter of the photocell.

3. A fiber optic light detector as claimed in claim 1, wherein the first and second stationary pegs are positioned on the periphery of the photocell.

4. A fiber optic light detector as claimed in claim 1, wherein the first and second stationary pegs are positioned slightly outwardly spaced from the periphery of the photocell.

5. A fiber optic light detector as claimed in claim 1, wherein said first and second stationary pegs are arcuately spaced apart from between 15° and 60°.

6. A fiber optic light detector as claimed in claim 1, wherein the photocell is of a size which is able to produce an accurate light intensity reading for all fiber optic bundles having a diameter equal to and greater than the diameter of the photocell.

7. In combination, a fiber optic light detector and a curing light, wherein the fiber optic light detector comprises:
    a housing;
    a photocell, positioned within the housing for sensing a light emitted from the curing light and determining the intensity of the light;
    a light intensity display, positioned within the housing and connected to the photocell, for displaying the intensity determined by the photocell; and
    first and second stationary pegs, integral with the housing and spaced about the circumference of the photocell, against which a fiber optic bundle is removably positioned to thereby completely cover the photocell when determining the intensity of the light emitted by the curing light; and
    the curing light comprises:
    a halogen lamp for creating a light of a desired intensity to be measured by the photocell; and
    a fiber optic positioned for illumination by the halogen lamp.

8. The combination as claimed in claim 7, wherein the first and second pegs are positioned about the photocell such that the distance between the first and second pegs is less than the diameter of the photocell.

9. The combination as claimed in claim 7, wherein the first and second stationary pegs are positioned on the periphery of the photocell.

10. The combination as claimed in claim 7, wherein the first and second stationary pegs are positioned slightly spaced from the periphery of the photocell.

11. The combination as claimed in claim 7, further comprising a power source connected to both the detector and curing light for supplying power to both the detector and curing light.

12. The combination as claimed in claim 7, wherein the curing light further comprises a first thermal switch for turning the halogen lamp off when the temperature within the curing light reaches a first threshold value.

13. The combination as claimed in claim 7, wherein the curing light further comprises a first thermal switch for turning the halogen lamp off after the curing light has operated for a predetermined maximum amount of time.

14. The combination as claimed in claim 7, wherein the curing light further comprises a fan for cooling the curing light from heat generated by the halogen lamp.

15. The combination as claimed in claim 14, wherein the curing light further comprises a second thermal switch for supplying voltage to the fan after the halogen lamp has been turned off, and for turning the fan off when the temperature inside the curing light reaches a second threshold value.

16. The combination as claimed in claim 7, further including a timer having a dial control, connected to the halogen lamp, for delivering voltage to the halogen lamp for a period of time and turning the halogen lamp off once that time has expired.

17. The combination as claimed in claim 7, wherein the photocell is of a size which is able to produce an accurate light intensity reading for curing lights connected with a fiber optic bundle and having a diameter equal to or greater than the diameter of the photocell.

18. The combination as claimed in claim 7, wherein the housing further includes a cradle extending therethrough for securing the curing light.

19. The combination as claimed in claim 7, wherein the curing light further includes a trigger for activating and deactivating the curing light when depressed.

20. The combination as claimed in claim 18, wherein the curing light further includes an audible indicator connected to the trigger for producing an audible signal each time the trigger is depressed, indicating activation and deactivation of the curing light.

* * * * *